United States Patent [19]
Houser et al.

[11] Patent Number: 6,074,351
[45] Date of Patent: *Jun. 13, 2000

[54] VARIABLE CURVE ELECTROPHYSIOLOGY CATHETER

[75] Inventors: Russell A. Houser, Livermore; Tom Bourne, Mountain View, both of Calif.

[73] Assignee: EP Technologies, Inc., San Jose, Calif.

[*] Notice: This patent is subject to a terminal disclaimer.

[21] Appl. No.: 09/111,168

[22] Filed: Jul. 7, 1998

Related U.S. Application Data

[63] Continuation of application No. 08/713,101, Sep. 16, 1996, Pat. No. 5,928,191, which is a continuation of application No. 08/378,530, Jan. 26, 1995, abandoned, which is a division of application No. 08/099,843, Jul. 30, 1993, Pat. No. 5,397,321.

[51] Int. Cl.$^7$ ........................................................ A61B 5/00
[52] U.S. Cl. ................................ 600/585; 606/41; 604/95
[58] Field of Search ................................... 606/1, 41, 45, 606/50; 607/115, 116, 122; 604/95, 280, 282; 600/585

[56] References Cited

U.S. PATENT DOCUMENTS

| | | |
|---|---|---|
| 3,605,725 | 9/1971 | Bentov . |
| 4,245,624 | 1/1981 | Komiya . |
| 4,273,111 | 6/1981 | Tsukaya . |
| 4,586,923 | 5/1986 | Gould et al. . |
| 4,676,249 | 6/1987 | Arenas et al. . |
| 4,677,990 | 7/1987 | Neubauer . |
| 4,873,983 | 10/1989 | Winters . |
| 4,886,067 | 12/1989 | Palermo . |
| 4,909,787 | 3/1990 | Danforth . |
| 4,917,102 | 4/1990 | Miller et al. ............................ 128/772 |
| 4,920,980 | 5/1990 | Jackowski . |
| 5,010,894 | 4/1991 | Edhag . |
| 5,040,543 | 8/1991 | Badera et al. .......................... 128/772 |
| 5,055,101 | 10/1991 | McCoy . |
| 5,083,565 | 1/1992 | Parins . |
| 5,108,368 | 4/1992 | Hammerslag et al. . |
| 5,170,787 | 12/1992 | Lindegren . |
| 5,190,050 | 3/1993 | Nitzsche . |
| 5,203,772 | 4/1993 | Hammerslag et al. . |
| 5,228,441 | 7/1993 | Lundquist . |
| 5,231,989 | 8/1993 | Middleman et al. . |
| 5,254,088 | 10/1993 | Lundquist et al. . |
| 5,255,668 | 10/1993 | Umeda . |
| 5,273,535 | 12/1993 | Edwards et al. . |
| 5,275,151 | 1/1994 | Shockey et al. . |
| 5,306,245 | 4/1994 | Heaven . |
| 5,330,466 | 7/1994 | Imran . |
| 5,357,979 | 10/1994 | Imran . |
| 5,364,352 | 11/1994 | Cimino et al. . |
| 5,389,072 | 2/1995 | Imran . |
| 5,389,073 | 2/1995 | Imran ....................................... 604/95 |
| 5,391,147 | 2/1995 | Imran et al. . |
| 5,397,321 | 3/1995 | Houser et al. . |
| 5,423,771 | 6/1995 | Imran . |
| 5,478,330 | 12/1995 | Imran . |
| 5,487,757 | 1/1996 | Truckai et al. . |
| 5,533,967 | 7/1996 | Imran ....................................... 604/95 |
| 5,833,604 | 11/1998 | Houser et al. . |
| 5,928,191 | 7/1999 | Houser et al. . |
| 5,944,689 | 8/1999 | Houser et al. . |

FOREIGN PATENT DOCUMENTS 0 600 676   6/1994   European Pat. Off. .

*Primary Examiner*—Michael Peffley
*Attorney, Agent, or Firm*—Henricks, Slavin & Holmes LLP

[57] ABSTRACT

An electrode tip assembly attachable to the end of a catheter for supporting a tip electrode for percutaneous insertion into a living body having a steering mechanism includes an elongated body bendable in response to external forces to steer the tip electrode. The body is connected at its distal end to the tip electrode. At least one steering wire is attached to the elongated body for transmitting bending force to the body from a remote control mechanism. An movable stiffening member, preferably in the form of a sleeve or rod provides a variable fulcrum for bending of the body in response to an applied bending force. A control stylet or sleeve extends through the catheter and is attached to the stiffening member for moving the stiffening member in a distal/proximal direction or for rotating it relative to the body.

29 Claims, 3 Drawing Sheets

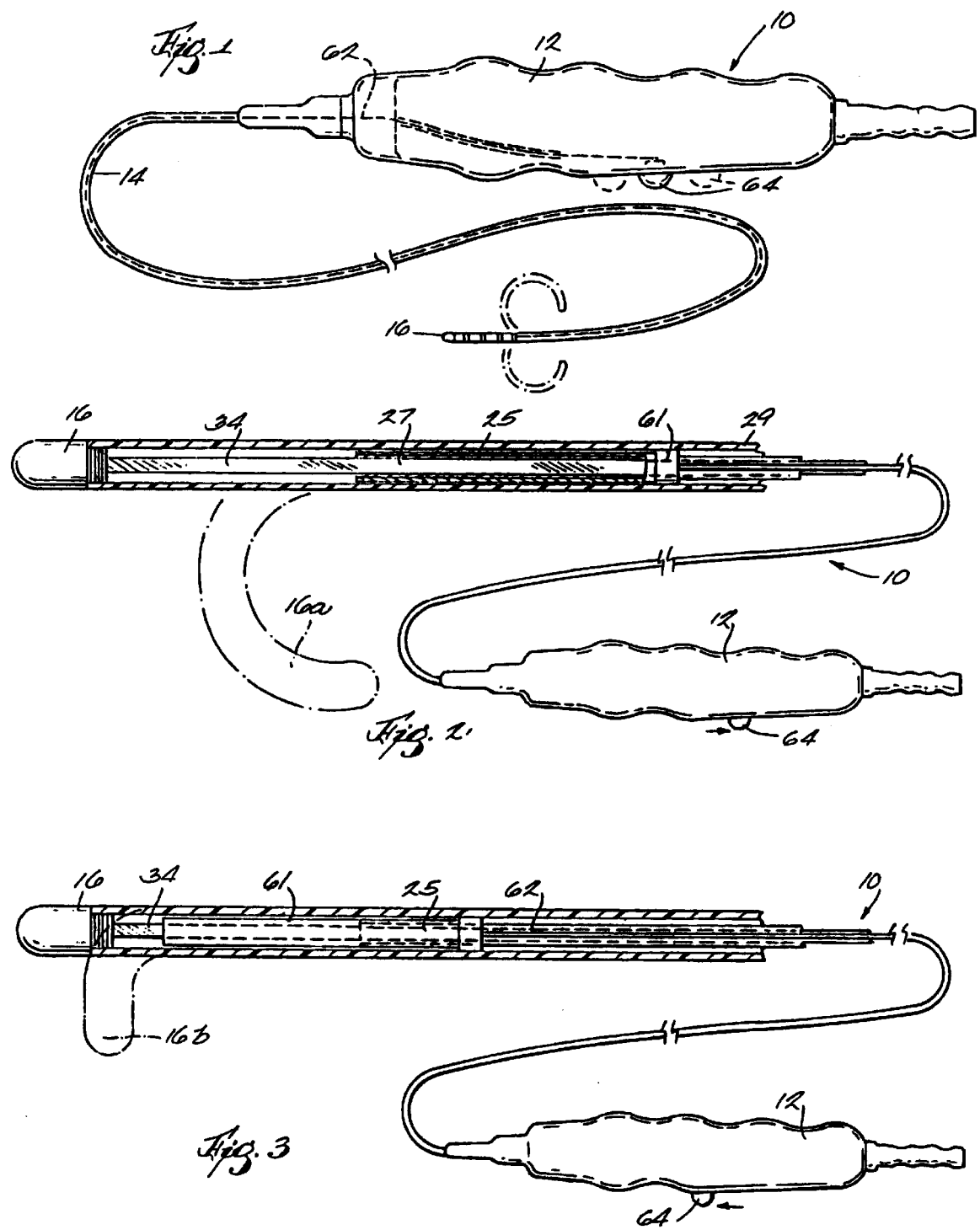

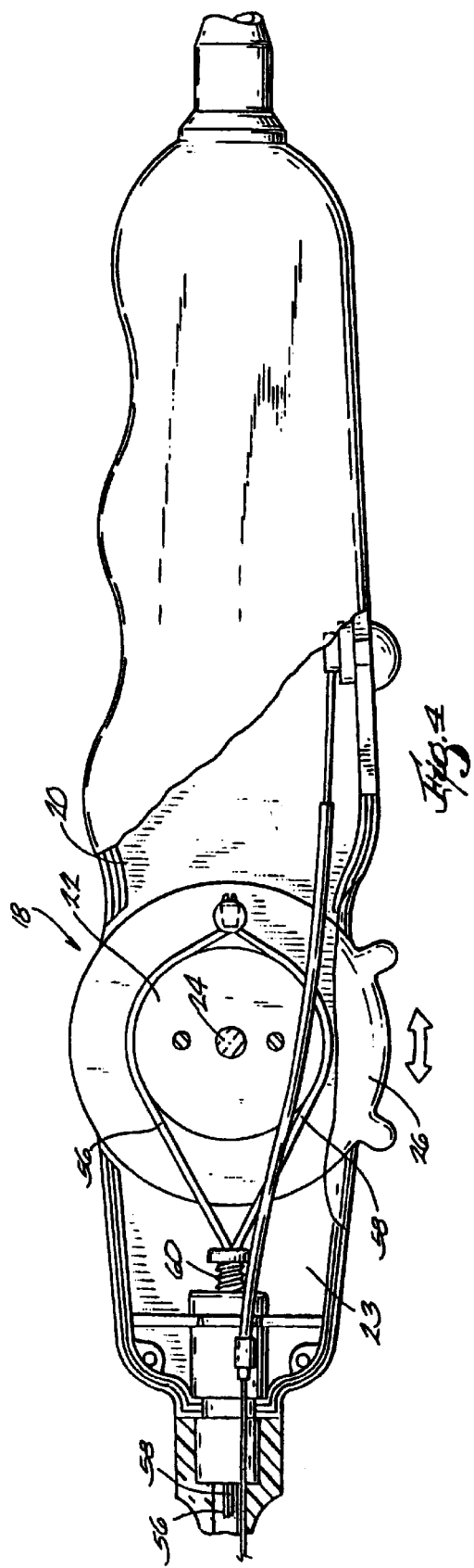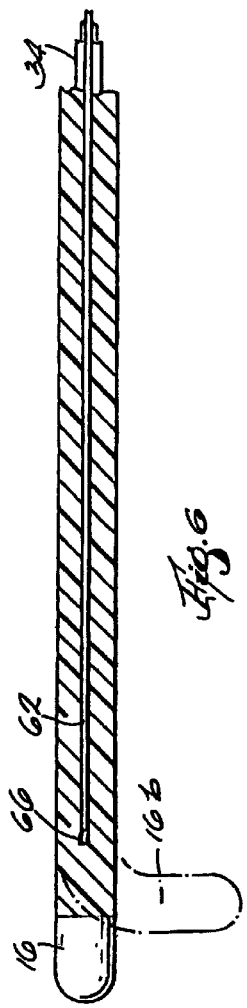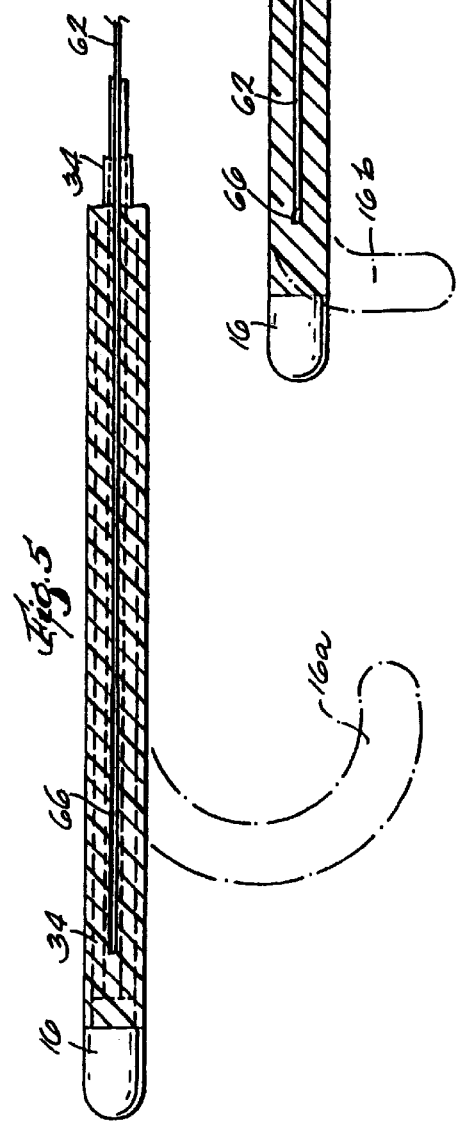

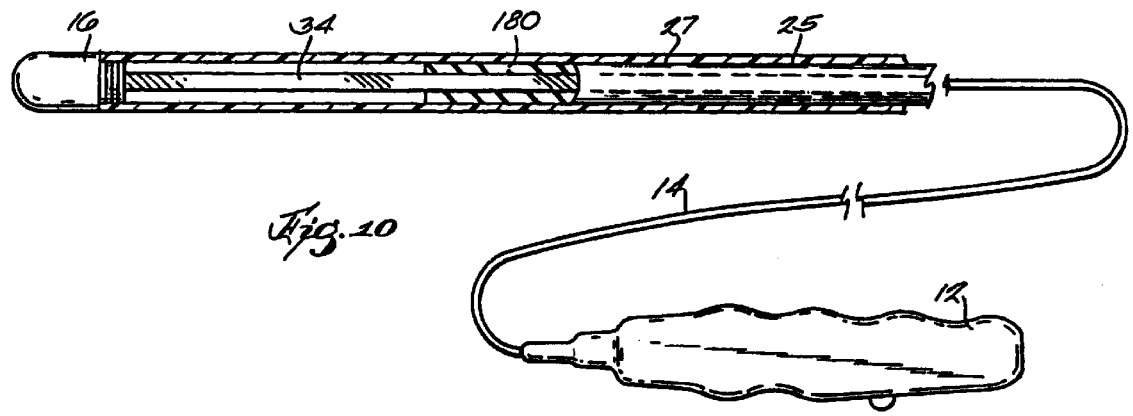
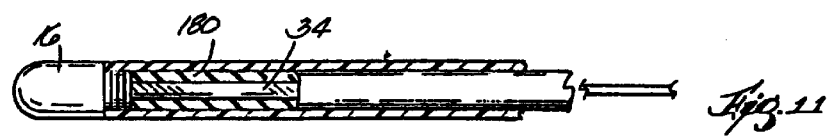
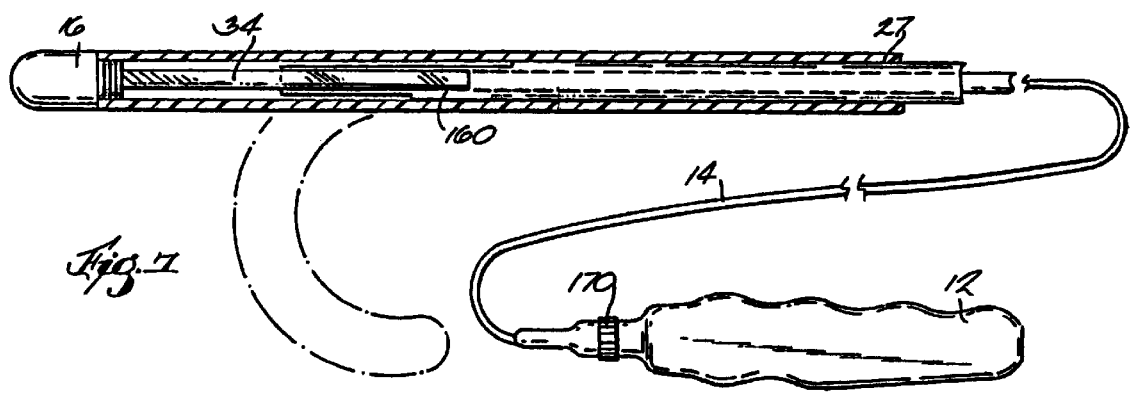
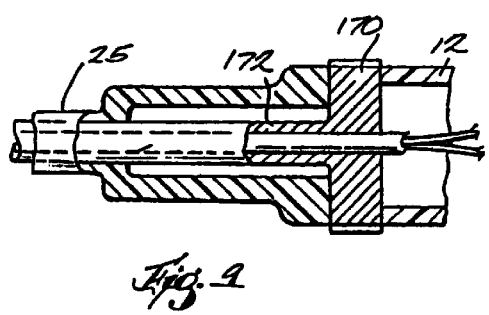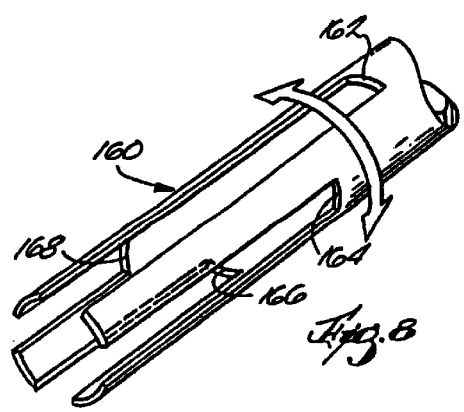

VARIABLE CURVE ELECTROPHYSIOLOGY CATHETER

This application is a continuation of U.S. application Ser. No. 08/713,101, filed Sep. 16, 1996, now U.S. Pat. No. 5,928,191, which is a continuation of U.S. application Ser. No. 08/378,530, filed Jan. 26, 1995, now abandoned, which is a divisional of U.S. application Ser. No. 08/099,843, filed Jul. 30, 1993, now U.S. Pat. No. 5,397,321.

FIELD OF THE INVENTION

This invention relates to catheters that can by steered by external controls.

BACKGROUND OF THE INVENTION

Cardiac mapping is used to locate aberrant electrical pathways and currents emanating within the heart. Such aberrant pathways cause irregular contractions of the heart muscle resulting in life-threatening patterns or disrhythmias.

Intercardiac mapping requires careful positioning of the electrodes within the heart. Various steering mechanisms for catheters carrying such electrodes have heretofore been developed and used.

To provide catheters having different curve configurations to access various endocardial sites, physicians have to stock and use number of different catheters, each of which provides a different curve configuration. Commercially available catheters, thus, come in sets, which often provide 4 to 7 different curve configurations by using different catheters.

This approach presents serious disadvantages, because the physician often must repeatedly remove and re-insert these different catheters to complete a procedure on a given patient.

A need exists for a catheter which could be steered into different curvatures without removing and re-inserting a different catheter.

SUMMARY OF THE INVENTION

The present invention provides a catheter, usable in both diagnostic and therapeutic applications, that enables a physician to swiftly and accurately change the configuration of the distal curve of the catheter as it is steered within the body of a patient. The catheter that embodies the invention allows physicians to access many more endocardium sites than heretofore achievable by a single catheter. In its broadest aspect, the invention provides a catheter which enables a physician to alter the physical characteristics of a catheter inserted within a living body by manipulation of external controls.

One aspect of the invention provides a catheter having an internal fulcrum that can be moved within the catheter to different distances relative to the distal tip by external manipulation. Movement of the internal fulcrum results in creating different curvature radii for bending of the distal tip.

The internal fulcrum that the invention provides is usable in connection with unidirectional catheters, as well as bi-directional, steerable catheters.

The invention provides a catheter in which a longer fulcrum-to-distal tip distance can be provided for accessing and measuring electrical activity in portions of the heart such as the coronary sinus, the right ventricular overflow tract and the HIS bundle. Similarly, a shorter fulcrum-to-tip distance can be used to access such areas as the high right atrium and the right and left ventricle apex of the heart.

An important advantage of the present invention is to provide a catheter which enables the physician to reduce the time required for a procedure by changing the type of curvature obtainable by the catheter while the catheter is still in the patient's body. A yet further aspect of the invention is to provide a catheter steering mechanism wherein a variable fulcrum is provided but wherein currently available steering components and mechanisms can be utilized.

In accordance with a still further aspect of the invention, a movable fulcrum within a catheter is provided by utilizing a stylet that can be proximally-distally manipulated and which is connected to an annular tube, the distal end of which forms a fulcrum within a catheter. A further related aspect is the ability to use such moveable tubes of different materials, having different rigidity characteristics. In this regard, a relatively rigid material can be used to provide an abrupt or short radius distal curvature of the catheter and a more pliable tube could be used, if desired, to produce a curve with more gradual characteristics or a larger radius. In accordance with still further aspects of the invention, it is possible to substitute a different slidable stiffening mechanism within the catheter, for example, a segment of a movable interior stiffening rod can be employed rather than an annular tube. In accordance with yet another embodiment of the invention the stiffening member is provided with a distal end having circumferential segments terminating at different distal positions relative to the steering body, thus enabling the changing of fulcrum points for bending of the steering body by rotating the stiffening member relative to the steering body. In this embodiment the stiffening member may be carried on the distal end of a rotatable sleeve positioned in the catheter.

Briefly summarized, the invention provides a catheter for percutaneous insertion into a living body having a steering mechanism that includes a n elongated body bendable in response to external forces to steer the catheter tip. The body has a proximal end for attachment to a guide tube Located within the body of the catheter and a distal end for carrying an operative element such as a tip electrode. At least one steering wire is attached to the elongated body for transmitting bending force to the body from a remote control mechanism. An axially movable stiffening member, preferably in the form of an axially or rotationally movable sleeve or rod provides a variable fulcrum for bending of the body in response to an applied bending force. A control stylet or wire extends through the length of the catheter body and is attached to the stiffening member for moving the stiffening member in a distal/proximal direction.

Further, objects and advantages of the invention will become apparent from the following detailed description and accompanying drawings.

BRIEF DESCRIPTION OF DRAWINGS

FIG. 1 is a top view of a catheter and catheter handle assembly in accordance with the invention with some interior parts shown by means of phantom lines;

FIG. 2 is a view of the catheter shown in FIG. 1 with the tip portion broken away and shown in cross-section on a greatly enlarged scale and showing a moveable sleeve in a proximal position;

FIG. 3 is a view in accordance with FIG. 2 showing the sleeve in a more distal position;

FIG. 4 is a top sectional view of the handle of the device of the present invention on a greatly enlarged scale;

FIG. 5 is a sectional view of a tip portion of a catheter in accordance with another embodiment of the invention;

FIG. 6 is a view of the device of FIG. 5 with the curve adjusting mandrel advanced to a more distal position;

FIG. 7 is a view of a catheter showing an alternate embodiment of the invention utilizing a rotatable sleeve;

FIG. 8 is a perspective view showing the configuration of the distal end of the sleeve of the device shown in FIG. 7;

FIG. 9 is a fragmentary cross-sectional view showing the control mechanism in the distal portion of the handle of the handle of the catheter of FIG. 7;

FIG. 10 is a view of a catheter showing bendable axially movable stiffening member in a retracted approximal position, and;

FIG. 11 is a sectional view of the distal tip portion of the catheter of FIG. 10 with the stiffening member advanced to its most distal position.

DETAILED DESCRIPTION OF PREFERRED EMBODIMENTS

FIG. 1 shows a steerable catheter 10 that embodies the features of the invention. The catheter 10 includes several main parts: a handle 12, a catheter tube or body 14, and a steerable distal tip assembly 16. In use, the catheter 10 provides electrophysiology diagnosis or therapy in the interior regions of the heart.

When used for this purpose, a physician grips the handle 12 and maneuvers the catheter body 14 through a main vein or artery (which is typically the femoral vein) into the interior region of the heart that is to be treated. The physician then further steers the distal tip assembly 16 to place it in contact with the tissue that is to be ablated. The physician directs energy to an electrode in the assembly 16 to ablate the tissue contacted.

As FIG. 4 shows, the handle 12 encloses a steering mechanism which may be in the form of a rotating cam wheel of the type shown in U.S. Pat. No. 5,195,968. While one form of steering mechanism 18 is shown for purposes of illustration, it will be understood that many other mechanisms that allow for selective pulling of the steering wires in the catheter can be substituted.

As FIG. 4 best shows, the handle assembly 12 includes a housing 20 that encloses the steering mechanism 18. The steering mechanism 18 includes a rotatable wheel or cam 22 carried on a shaft 24 within the housing 20. The rotatable cam 22 and control knob 26 are attached to shaft 24 by splines. Clockwise movement of the control knob 26 rotates the cam 22 clockwise pulling on wire 56. Counterclockwise movement of the control knob 26 reverses the direction of each of these movements and results in pulling wire 58. Various other mechanisms can be substituted to apply tension to wires 56 and 58 in place of that shown in FIG. 4.

The steering wires 56 and 58 exit the front of the housing 20 through the interior bore of a tension screw assembly 60. The distal ends; of the steering wires 56 and 58 are attached to a steering wire or spring in the electrode tip assembly 16.

The catheter body 14 is a flexible shaft attached to the handle 12. While it can be variously constructed, in a preferred embodiment, the catheter body 14 is a length of stainless steel coiled into a flexible spring 25 enclosing an interior bore 27 which in turn is enclosed in a braided sheath 29 of plastic material. The steering wires 56 and 58 preferably pass through the interior bore 27, which leads to the distal tip assembly 16 where the steering wire are attached to a bendable main support wire 34. In the illustrated embodiment, the main support wire 34 is made of stainless steel flat wire stock in an elongated shape about 0.035 inch wide and about 0.005 inch thick. The main support wire 34 is about 3 inches in total length.

In the distal end of the catheter body 14 there is no surrounding sheath or shield, leaving the steering assembly exposed. Positioned in the distal end region and overlying the distal end of coil 25 is a curve adjusting tube 60. The proximal end of curve adjusting tube 60 is attached to a mandrel 62 that extends within the catheter body 14 into handle 12. The proximal end of mandrel 62 is connected to a slidable, bi-directional adjuster knob 64. Sliding of knob 64 enables the practitioner to slide the adjusting tube 60 axially within the catheter body 14 to a more proximal or more distal location as desired. The more proximal and more distal positions of knob 64 are shown in FIG. 1 by means of phantom lines. In the more proximal location illustrated in FIG. 2, the curve adjusting tube 60 is positioned to permit the maximum curvature of distal tip assembly 16 to position 16a illustrated by means of phantom lines. In the more distal location illustrated in FIG. 3, the tube 60, which acts as a slidable fulcrum for the tip, steering of the tip by means of knob 26 causes a shorter portion of the tip 16 to curve to a sharper curve illustrated by phantom lines 16b in FIG. 3.

In the alternate embodiment illustrated in FIGS. 5 and 6, the mandrel 62, which may be provided with an enlarged end section, is positioned for axial sliding within a channel 66 in similar to that shown in FIGS. 2 and 3 the distal tip 16 can be bent to different curvatures 16a or 16b as shown in FIGS. 5 and 6. It will readily be apparent that intermediate curve shapes other than those illustrated by lines 16a and 16b can be provided by positioning level 64 in an intermediate position.

In the preferred embodiment of the device shown in FIGS. 2 and 3 outer sleeve 29 is formed of Kevlar. Mandrel 62 is formed of a 0.02 inch stainless steel wire running parallel between the guide coil 25 and the inside of Kevlar tubing 29. Wire 64 is preferably attached on the outside of a 2.5 inch long 0.050 inch inter diameter 0.055 inch outer diameter length of tube that forms sleeve 60. The tube can be made of stainless steel, nitinol alloy or a polymeric material such as polyamide or other polymer. In the preferred embodiment, a polyamide tube is reinforced by a stainless steel coil embedded in the wall. To provide a well defined movable fulcrum the sleeve is formed of a rigid material. It will also be apparent that in the event the tube 60 is made from a relatively softer material or more flexible material such as a polyurethane, silicone, or polyethylene, it will provide a stiffening effect but have less effect on the changing of the curve radius of the tip.

In a further embodiment shown in FIGS. 7–9 a tube 160 is rotatable relative to the steering wire 34 rather than being axially movable relative thereto. In this case a rotatable sleeve concentric with spring 25 and located within bore 27 is attached to tube 160 for the purpose of applying rotational forces thereto. Tube 160 is provided with a distal end having circumferential segments 162, 164, 166, and 168 of differing lengths. Each of these circumferential segments provides a fulcrum or stiffening member spaced a different distance from the distal tip of the catheter and thus provides for as many different curvature shapes of the tip as there are segments.

Tube 160 is rotated by applying a force to control knob 170 located in handle 12. Tube 160 is connected to control handle 170 by means of a torque transmitting tube 172. Since the control wire 34 will tend to bend the distal tip 16 from side to side in a single plane, the fulcrum length provided by rotatable tube 160 is dependent on which of the segments 162, 164, 166 or 168 is positioned in the plane in which control wire 34 bends. Appropriate markings on handle 12 can be provided to indicate the position in which control knob 170 is rotated. Thus, the physician can readily change the fulcrum length or stiffness characteristics of the distal tip of the catheter by manually rotating knob 170.

In the embodiment of FIG. 10, a stiffening member 180 is shown in the form of a flexible polymeric tube. Any flexible material can be used as a material of construction for tube 180. A rod 62 of the type in FIGS. 5 and 6 is used as a stiffening member. Any flexible materials such as plastic, metal or other bendable materials of construction can be used.

Referring to FIGS. 10 and 11, when sleeve 180 is in the retracted position shown in FIG. 10, the tip 16 can be steered easily with greatly reduced resistance to bending when bending forces are applied to the tip by means of steering mechanism 18. When the stiffening member 180 is advanced to its most distal position shown in FIG. 11, the same catheter can behave as one that is stiffer or resistent to bending. By placing a flexible stiffening member in an intermediate position, it is possible to alter the curve characteristics of a catheter by stiffening a portion of the steerable tip portion but not the more distal portion thus providing a further range of possible curve configurations obtainable by the steerable catheter tip.

It will, thus, be appreciated that in accordance with the invention, the characteristics of the distal tip of a steerable catheter can be altered by means of movement of a remote control member. This alteration can occur when the catheter is being used within a living body. The invention, thus, makes possible the alteration of numerous characteristics of a catheter without the need for withdrawing the catheter from the body.

What is claimed is:

1. A probe, comprising:
   a probe body defining a distal end, a proximal end and a longitudinally extending bore;
   a tip associated with the distal end of the probe body, the tip defining a distal end and a proximal end and being adapted to bend relative to the probe body;
   a user actuatable steering control device operably connected to the tip and adapted to apply a bending force to the tip; and
   a stiffening member associated with the probe body and the tip and defining a free distal end that is not operably connected to the tip, at least a portion of the stiffening member being movable between the proximal end of the tip and at least a first position between the distal and proximal ends of the tip to selectively increase the stiffness of the portion of the tip occupied by the stiffening member.

2. A probe as claimed in claim 1, further comprising:
   a stiffening member control device associated with the proximal end of the probe body, operably connected to the stiffening member, and adapted to move the stiffening member relative to the tip.

3. A probe as claimed in claim 2, wherein the probe body defines a longitudinal axis and the stiffening member control device moves the stiffening member along the longitudinal axis of the probe body.

4. A probe as claimed in claim 2, wherein the stiffening member control device comprises a slideable knob.

5. A probe as claimed in claim 2, wherein the stiffening member control device is operably connected to the stiffening member by an elongate member.

6. A probe as claimed in claim 2, further comprising:
   a handle associated with the proximal end of the probe body;
   wherein the stiffening member control device is located on the handle.

7. A probe as claimed in claim 1, wherein the steering control device is operably connected to the tip by a control wire extending from the tip to the steering control device.

8. A probe as claimed in claim 1, further comprising:
   a handle associated with the proximal end of the probe body;
   wherein the steering control device is located on the handle.

9. A probe as claimed in claim 1, wherein the stiffening member comprises an elongate stiffening member slidable within the longitudinally extending bore in the probe body.

10. A probe as claimed in claim 1, wherein the stiffening member comprises a substantially tubular stiffening member.

11. A probe as claimed in claim 10, wherein the probe body comprises an elongate flexible tube and the substantially tubular stiffening member is positioned around the elongate flexible tube.

12. A probe as claimed in claim 11, wherein the elongate flexible tube comprises a coil.

13. A probe as claimed in claim 1, further comprising:
    an electrode associated with the tip.

14. A probe as claimed in claim 1, wherein the tip comprises a steering spring.

15. A probe as claimed in claim 1, wherein the stiffening member increases the stiffness of the tip at the first position when moved to the first position.

16. A probe, comprising:
    a probe body defining a distal portion and a proximal portion;
    a user actuatable steering control device operably connected to the distal portion of the probe body and adapted to apply a bending force to the distal portion of the probe body; and
    a stiffening member having at least a portion thereof movable between at least a first position along the distal portion of the probe body and a second position along the distal portion of the probe body distal of the first position, the stiffening member increasing the stiffness of the probe body at the second position when located at the second position without effecting the stiffness of the probe body distal to the second position.

17. A probe as claimed in claim 16, further comprising:
    a stiffening member control device associated with the proximal portion of the probe body, operably connected to the stiffening member, and adapted to move the stiffening member relative to the distal portion of the probe body.

18. A probe as claimed in claim 17, wherein the probe body defines a longitudinal axis and the stiffening member control device moves the stiffening member along the longitudinal axis of the probe body.

19. A probe as claimed in claim 17, wherein the stiffening member control device comprises a slideable knob.

20. A probe as claimed in claim 17, wherein the stiffening member control device is operably connected to the stiffening member by an elongate member.

21. A probe as claimed in claim 17, further comprising:
    a handle associated with the proximal portion of the probe body;

wherein the stiffening member control device is located on the handle.

22. A probe as claimed in claim 16, wherein the steering control device is operably connected to the distal portion of the probe body by a control wire extending from the distal portion of the probe body to the steering control device.

23. A probe as claimed in claim 16, further comprising:
a handle associated with the proximal portion of the probe body;
wherein the steering control device is located on the handle.

24. A probe as claimed in claim 16, wherein the probe body defines a longitudinally extending bore and the stiffening member comprises an elongate stiffening member slidable within the longitudinally extending bore.

25. A probe as claimed in claim 16, wherein the stiffening member comprises a substantially tubular stiffening member.

26. A probe as claimed in claim 25, wherein the probe body comprises an elongate flexible tube and the substantially tubular stiffening member is positioned around the elongate flexible tube.

27. A probe as claimed in claim 26, wherein the elongate flexible tube comprises a coil.

28. A probe as claimed in claim 16, further comprising:
an electrode associated with the distal portion of the probe body.

29. A probe as claimed in claim 16, wherein the distal portion of the probe body includes a steering spring.

* * * * *